US012558097B2

(12) United States Patent
Brijawi

(10) Patent No.: US 12,558,097 B2
(45) Date of Patent: Feb. 24, 2026

(54) DEVICE FOR APPLYING RUBBER BANDS IN THE HUMAN BODY

(71) Applicant: Loai Brijawi, Ludwigshafen (DE)

(72) Inventor: Loai Brijawi, Ludwigshafen (DE)

( * ) Notice: Subject to any disclaimer, the term of this patent is extended or adjusted under 35 U.S.C. 154(b) by 383 days.

(21) Appl. No.: 18/034,593

(22) PCT Filed: Oct. 25, 2021

(86) PCT No.: PCT/EP2021/079576
§ 371 (c)(1),
(2) Date: Apr. 28, 2023

(87) PCT Pub. No.: WO2022/090176
PCT Pub. Date: May 5, 2022

(65) Prior Publication Data
US 2023/0329717 A1    Oct. 19, 2023

(30) Foreign Application Priority Data

Oct. 29, 2020    (DE) ......................... 102020213617.3

(51) Int. Cl.
*A61B 17/12*    (2006.01)
*A61B 90/00*    (2016.01)
A61B 17/00    (2006.01)

(52) U.S. Cl.
CPC ........ *A61B 17/12013* (2013.01); *A61B 90/03* (2016.02); *A61B 2017/00296* (2013.01);
(Continued)

(58) Field of Classification Search
CPC .......... A61B 2017/12018; A61B 90/03; A61B 2090/031; A61B 2090/032;
(Continued)

(56) References Cited

U.S. PATENT DOCUMENTS 5,693,059 A * 12/1997 Yoon ................ A61B 17/12013
606/139
5,843,091 A * 12/1998 Holsinger ......... A61M 25/0026
604/48
(Continued)

FOREIGN PATENT DOCUMENTS

CN    210144714 U    3/2020
DE    299129454 U1    9/2000
(Continued)

OTHER PUBLICATIONS

German Office Action 10 2020 213 617.3 dated Jul. 26, 2021, 7 pages.
(Continued)

*Primary Examiner* — Darwin P Erezo
*Assistant Examiner* — Mitchell Brian Hoag
(74) *Attorney, Agent, or Firm* — Carter, DeLuca & Farrell LLP

(57)    ABSTRACT

A device for applying rubber bands in the human body and in other living beings includes: an axial element having a first handle; a trigger movably mounted on the axial element having one or more handles for moving the trigger along the axial element wherein the trigger serves to pull a wire; and an assembly that has a spool for winding up the wire. The spool is tightly connected with the trigger by a gear mechanism formed in such a way that, when the trigger is pulled, the spool is not rotationally driven and the wire is pulled along by way of the pulling movement of the trigger, whereby one or more rubber bands can be applied to a part of a living being to be treated, and that when the trigger moves back into a starting position, the wire is wound onto the spool.

16 Claims, 10 Drawing Sheets

(52) U.S. Cl.
CPC ............... *A61B 2017/00407* (2013.01); *A61B 2017/12018* (2013.01); *A61B 2090/035* (2016.02)

(58) Field of Classification Search
CPC ........... A61B 2017/00318; A61B 2017/00323; A61B 34/70; A61B 34/71; A61B 2034/715; A61B 2010/0208; A61B 2017/00367; A61B 2090/035; A61B 2090/034; A61B 2090/033; A61B 17/32056; A61B 17/12013; A61B 17/12009; A61B 2017/12004; A61B 17/12

See application file for complete search history.

(56) References Cited

U.S. PATENT DOCUMENTS

| | | | | |
|---|---|---|---|---|
| 6,007,551 | A * | 12/1999 | Peifer | .............. A61B 17/12013 |
| | | | | 606/139 |
| 6,443,943 | B1 * | 9/2002 | Ouchi | ................ A61B 17/2909 |
| | | | | 606/1 |
| 7,063,661 | B2 | 6/2006 | Okada | |
| 7,789,825 | B2 * | 9/2010 | Nobis | ................ A61B 17/2909 |
| | | | | 606/1 |
| 9,277,959 | B2 * | 3/2016 | Okada | ................ A61B 18/1492 |
| 9,693,779 | B2 | 7/2017 | Wolfe | |
| 2002/0072757 | A1 * | 6/2002 | Ahmed | ............ A61B 17/12013 |
| | | | | 606/139 |
| 2008/0183035 | A1 | 7/2008 | Vakharia et al. | |
| 2011/0077666 | A1 * | 3/2011 | McCahon | ........ A61B 17/12013 |
| | | | | 606/139 |
| 2012/0095507 | A1 | 4/2012 | White et al. | |
| 2015/0066056 | A1 * | 3/2015 | Cabrera Aquino | .......................... |
| | | | | A61B 17/12013 |
| | | | | 606/140 |
| 2017/0202555 | A1 * | 7/2017 | Noda | ............... A61B 17/12013 |
| 2019/0008537 | A1 * | 1/2019 | Kirstgen | ............ A61B 17/2909 |
| 2021/0298760 | A1 * | 9/2021 | Tal | ...................... A61B 17/0482 |
| 2024/0173027 | A1 * | 5/2024 | Le | ...................... A61B 17/0487 |
| 2024/0215999 | A1 * | 7/2024 | Bartinelli, Jr. | ......... A61B 34/37 |

FOREIGN PATENT DOCUMENTS

| | | |
|---|---|---|
| DE | 102004002692 A1 | 8/2004 |
| EP | 1484077 A2 | 12/2004 |
| WO | 2006136053 A1 | 12/2006 |

OTHER PUBLICATIONS

International Search Report PCT/EP2021/079576 dated Jan. 27, 2022; 5 pages.

* cited by examiner

DEVICE FOR APPLYING RUBBER BANDS IN THE HUMAN BODY

The invention relates to a device, in particular for applying rubber bands in the human body and in other living beings with a rubber band ligature, which has a manually movable trigger.

GENERAL PRIOR ART

Rubber band ligatures, or also known as rubber ligatures, refers to a medical method for treating different diseases in the gastrointestinal tract, like vascular varices (such as oesophageal varices), arteriovenous vascular cushion (like hemorrhoids) or also in the context of the polypectomy for protection against bleeding. With oesophageal varices, the rubber band ligature is the treatment of choice, especially where there is active, recent or threat of bleeding.

For Grade 1 hemorrhoids, the method is an alternative to sclerotherapy. For the treatment of hemorrhoids, especially Grade 2 ones, this method seems ideal. Due to the low chances of success for third-grade haemorrhoids, this is generally only resorted to if there are important grounds against operating.

In rubber band ligatures, a rubber band is applied, via an applicator, to the bottom of the varices, haemorrhoids or polyp. This cuts off the protruding, prolapsing part and suppresses the local blood flow. When treating haemorrhoids or varices, after two to three days this results in a complete thrombotic occlusion of the vessel. After a few days, the cut-off part of the tissue dies and is excreted unnoticed, along with the rubber band, during bowel movements.

With up to ten rubber bands on the tip of the endoscope, several varices strands can be treated in one endoscopic session, and thus a complete ligation can be achieved. Occasionally, the remaining varices must be ligated in a second session.

The method is affordable and, in certain situations, relatively simple to carry out on outpatients. Normally, the treatment creates no pain, so that no anaesthetic is necessary.

The modern rubber band ligature was introduced in the 1950s by Blaisdell and was later developed further and technically refined by Barron, in that he introduced a mechanical instrument, the Barron ligator.

Further, a ligator is known (U.S. Pat. No. 9,693,779B2) that is provided for use with an endoscope, in order to be attached to a body of the endoscope. In the currently known treatment methods, several elastic bands are applied to the intestinal tissue one after another. To this end, an activation mechanism is used, which is supported by the body of the ligator. The activation mechanism comprises a rotatable activation button, a rotatable winding ring for the cord, an activation cord and a restriction member, which limits the rotation of the activation button between a starting position and an end position, beyond which no further rotation is possible. The handling of the device is very time-consuming.

Further devices for applying rubber bands in the human body are furthermore known form DE 299 12 945 U1, DE 10 2004 002 692 A1, US 2012/0095 507 A1, EP 1 484 077 A2 and US 2008/1 183 035 A1.

In the currently known rubber band ligators, the handle or the rubber band ligator is rotated manually and a negative reverse force is thus generated which leads to the destabilisation of the device.

The object of the invention is to simplify and automate the handling of the rubber band ligator as far as possible, since, with the help of the mechanism according to the invention, the rubber bands are released from the rubber band ligator.

The object is solved according to the invention by means of a device for applying rubber bands with the following features:

a) an axial element having a first handle;

b) a trigger, which is movably mounted on the axial element and has at least one handle for moving the trigger along the axial element, wherein the trigger serves to pull a wire;

c) an assembly that has a spool for winding up the wire.

According to an embodiment of the invention, the spool is coupled with the trigger by means of a gear mechanism, which implements a translational movement of the trigger during a rotational movement of the spool and is configured such that the spool is driven, at least during a part of the movement of the trigger along the axial element, and winds up the wire. During another part of the movement of the trigger, the spool is preferably not driven rotationally.

Instead of the previously mentioned gear mechanism, a spring-actuated winding mechanism can also be provided that can rotationally drive the spool. The spring-actuated winding mechanism can, for example, be designed in such a way that the wire is wound up while the trigger moves back from a proximal position into a distal starting position.

The gear mechanism can be designed in such a way that the spool can only be rotationally driven when the trigger is pulled from a distal position (starting position) into a proximal position, but not when it is returned into the starting position. Likewise, the gear mechanism can also be designed in such a way that the spool is rotationally driven when the trigger is returned into the starting position, but not when the trigger is pulled from the distal position (starting position) into the proximal position.

Regarding the arrangement of the assembly with the spool, there are different possibilities: in a first embodiment, the assembly is tightly connected with the spool with the trigger. In this case, the gear mechanism is preferably formed in such a way that, when the trigger is pulled, the spool is only moved with it without being rotationally driven, whereby the wire is correspondingly pulled along and one or more rubber bands can be applied to a part of a living being to be treated. When the trigger moves back into the starting position, the spool is rotationally driven by means of the movement of the trigger, and the wire is wound onto the spool.

The selective function of the gear mechanism, i.e. the selectively rotating drive of the spool during the pulling or the returning movement, can, for example, be achieved in that a toothed gearing of the gear mechanism is mechanically engaged during one movement and is mechanically disengaged during the other movement. The gear mechanism could, however, also comprise a form of pawl mechanism, which causes the pawl to engage with a corresponding element when the trigger is actuated in a first direction of movement, and the spool is rotationally driven, but is idle and exerts no force when the trigger is actuated in the opposite direction of movement.

According to a second embodiment, the assembly is arranged with the spool on the axial element. In this case, the trigger is preferably designed in such a way that it takes the wire with it from a distal position into a proximal position during the pulling of the trigger. The trigger can, for example, have a hook or catch for this purpose, which engages with the wire or is redirected. The gear mechanism is preferably designed in such a way that it rotationally drives the spool when returning the trigger from the proximal position into the starting position, but not when pulling the trigger. Regarding the selective function of the gear mechanism, the aforementioned applies.

The device for applying rubber bands can comprise an automatic winding mechanism, with the help of which the wire can be automatically tensioned in an initial stage of the application. The winding mechanism preferably comprises a spring, which rotationally drives the spool. Instead of a spring, another actuator, like e.g. an electric motor can also be provided.

The automatic winding mechanism is preferably locked in the starting position of the trigger, i.e. no pulling force is exerted on the wire. The automatic winding mechanism can be activated by means of releasing a lock. Accordingly, the spring or the actuator rotationally drives the spool, whereby the wire is pretensioned.

A significant advantage of the invention is that, with the help of the rubber band ligator, an automatic winding of the wire onto the spool occurs. The automatic winding occurs by means of pulling the trigger.

In the rubber band ligator according to the invention, the rubber bands are hereby applied to the part to be treated by means of the pulling, tension-compression principle, of the trigger. The work of the surgeon or of the doctor is thereby significantly simplified and can be carried out in a time-saving manner. The device for applying rubber bands according to the invention can be used with or without an endoscope.

It is thereby advantageous that rubber band ligation can be carried out by means of the pressure of the thumb on the endoscope and by means of one-handed operation, and the rubber band ligator remains fixed.

It is hereby advantageous that the axial element has an upper longitudinal groove and a lower longitudinal groove, which are connected via connecting ducts and serve as guide tracks for bolts.

It is furthermore advantageous that the holders are fitted with the bolts that belong to the assembly, and the bolts are guided into the ducts and the connecting ducts of the axial element, wherein the back bolts are continuously guided into the upper longitudinal groove, while the two other bolts are guided into the lower and the upper longitudinal groove and the connecting ducts.

It is also advantageous that two receiving members that are parallel and run spaced apart from each other are connected with each other, wherein one receiving member has an axle on which the spool that the wire can be wound onto by means of an automatic winding mechanism during the preparatory stage and a drive connection during the operating stage is arranged.

It is also advantageous that the drive connection consists of a gear rack and a gear wheel, which is brought into initial mesh with the gear rack after adjusting the assembly. By means of returning the trigger to the starting position, the wire is wound onto the spool.

It is hereby advantageous that the axle arranged on the holder extends through an opening provided in the second holder, wherein, with the help of the axle that has the edge surfaces, a coil spring, which is connected to a socket with the help of a holder, is locked.

It is also advantageous that a pipe can be received and adjusted into the axial element, wherein the wire can be guided into the pipe and the pipe is mounted in an endoscope and connected to the axial element in such a way that, with the help of the wire, the elastic elements, in particular the rubber bands, can be applied to the desired part of a living being.

It is also advantageous that, by means of activating the winding mechanism or gently pulling the trigger, a locking device of the spool is removed from an abutment of a front part, wherein the spool is then rotated clockwise with the help of the pretensioned wound coil spring and the wire is automatically wound onto the spool.

It is also advantageous that, by means of returning the trigger to its starting position, the wire is wound onto the spool and two pawls of the front part are simultaneously pushed outwards, wherein the bolts return the pawls to their original state after going past the pawls and thus ensure that the bolts cannot be moved backwards in the upper longitudinal groove, but rather can be moved in the lower longitudinal groove through the connecting duct.

It should hereby be noted that the wire is designed in such a way that it protrudes a little from the endoscope.

It is advantageous that a cap is arranged on the end of the endoscope, on which numerous rubber bands are mounted.

It is also advantageous that the unloading of a rubber band onto the end of the endoscope occurs with the help of the wire, wherein, for unloading the rubber band, the wire covers a distance of approx. 40 mm and, to this end, is wound onto the spool by means of returning the trigger to the starting position.

It should hereby be noted that, in a preparatory stage, the end of the wire is connected by means of a loop with a loop of a thread which is received in the endoscope, wherein, by means of gently pulling the trigger, the winding mechanism is operated and, as a result, the wire is drawn into the endoscope and the cap is placed on the end of the endoscope.

What characterises this rubber band ligator is the automatic winding mechanism, which ensures that the wire is quickly wound up and mounted during the preparatory stage with the help of a pretensioned, wound coil spring, which saves time and effort.

In the newly developed rubber band ligator, the rubber bands can be continuously released by means of a rack and pinion mechanism, with the help of a wire.

In contrast to current rubber band ligators, in which the handle effects a negative reverse force by means of the manual rotational movement, which leads to the destabilisation of the device, the rubber bands are released by means of pulling, i.e. tension-compression principle, the trigger by the rubber band ligator according to the invention.

As has been described at the start, the length of the path of the trigger (in the proximal direction) determines the length of the wound wire. The length of the path of the trigger is, as standard, limited by a proximal stop at a specific value, e.g. 35 mm-45 mm. In order to be able to use rubber bands of different types and sizes, the application of which requires different length paths, a stopper can be provided that limits the path of the trigger during the returning movement. In one embodiment, a stopper element can, for example, be provided, which can be fixed. e.g. attached to a desired place along the axial element. In another embodiment, e.g. one or more elements provided on the axial element e.g. pegs, can be provided, which can be adjusted by hand and either block or unblock a further movement of the trigger in the proximal direction.

For supporting the current application, in which different caps with different diameters are used, coils can also be used for winding, which have different regions with different diameters. The different diameters can be colour-coded for better allocation for using a specific cap. Alternatively, different, exchangeable coils can also be provided, each with only one specific diameter, which can in turn be colour-coded for the corresponding use.

Further advantages and details of the invention are explained in the claims and in the description, and shown in the figures.

Here:

Figure 1:
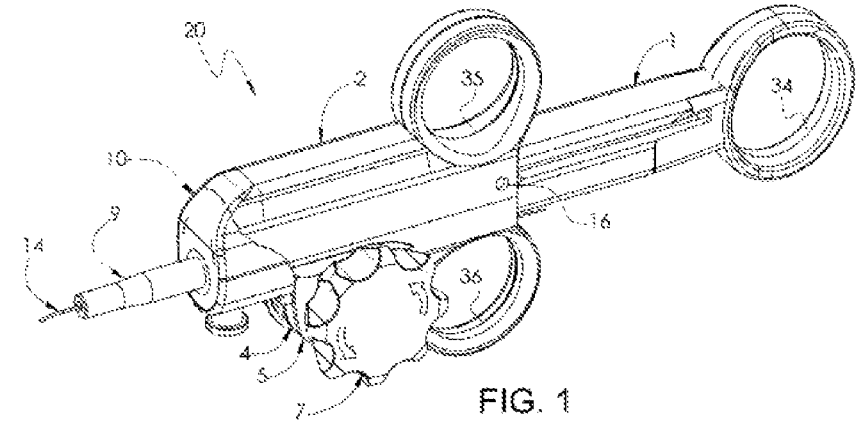
FIG. 1 shows a perspective representation of the rubber band ligator.

FIGS. 1 and 6 to 8 show a rubber band ligator with an automatic winding mechanism, which ensures that the excess length of a wire 14 and of a thread 53 can be wound up in a time-saving manner with the help of a pretensioned, wound coil spring 13 during the preparatory stage. The winding mechanism is formed, according to FIG. 5a, 5b among others, by the spool 4, the pretensioned coil spring 13, the locking device 25, the receiving members 3 and 5, the one-way needle bearing 12, the abutment 37 of the front part 10, as well as the socket 6.

Figure 20:
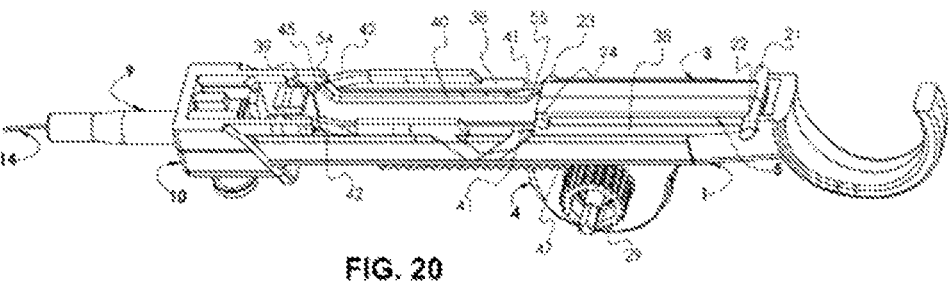
FIG. 20 shows a perspective sectional view of the rubber band ligator, wherein the end of the pulling stage of the wire is shown.

FIG. 1, 1a, 2, 3 and also FIG. 20 are perspective views of the rubber band ligator 20, which consists of an axial element 1, on one end of which a circular handle 34 is arranged, on which e.g. the thumb of a surgeon can be received, wherein two further circular handles 35, 36 are provided on the movable trigger 2, which is arranged movably on the axial element 1. An index finger and middle finger of a surgeon can be received into both handles 35, 36, which are arranged next to each other, and the trigger 2 can thereby be operated and moved onto the axial element 1 and thus, as explained further in the following, a rubber band 18 is applied to the bottom of the hemorrhoid, varices or polyp by the rubber band ligator 20.

Figure 5:
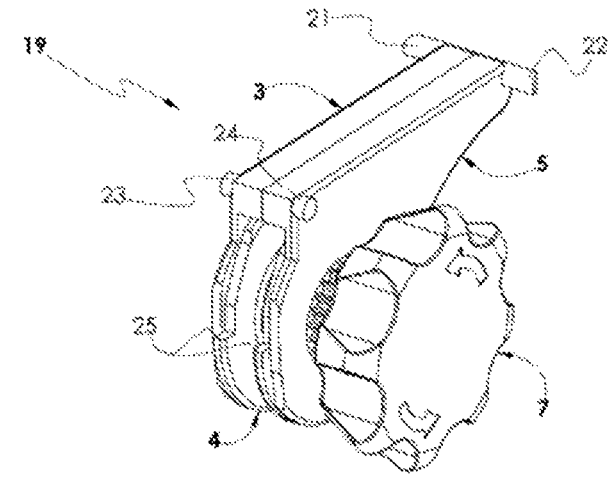
FIG. 5 shows an assembly.
Figure 5A:
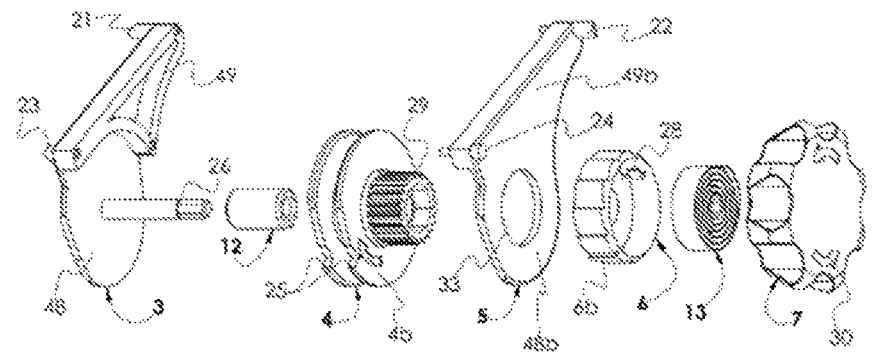
FIG. 5a, 5b show an exploded view of the assembly.
Figure 5B:
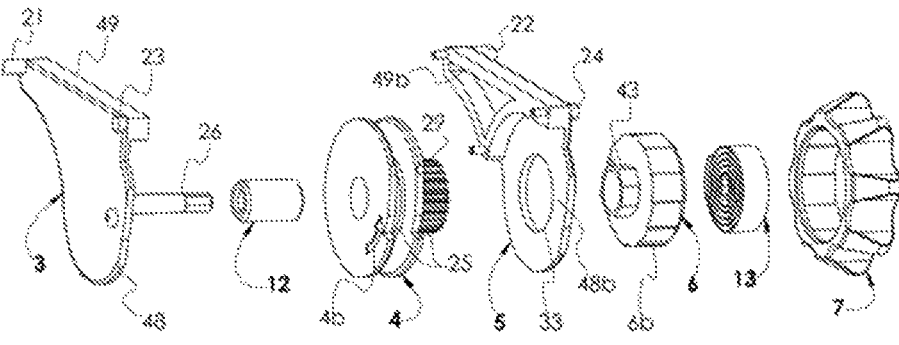

According to FIG. 5-5b of the perspective and the exploded view, the assembly 19 consists of the receiving members 3, 5 that are connected with each other, one being provided with a disc 48 and an axle 26, and the other being provided with a perforated disc 48b and an opening 33.

Locked on the axle 26 is a one-way needle bearing 12, on which a spool 4, which can only be rotated clockwise, according to arrow 4b, is mounted. A socket 6 is mounted on the spool 4 with the help of edge surfaces 43, which socket receives a wound coil spring and is mounted and pretensioned with the help of the handle 7.

To this end, the spool 4 has a locking device 25 on the outer circumference, which prevents a rotation without activating the automatic winding mechanism.

According to FIG. 5a, 5b, a gear wheel 29 is arranged on the spool 4 on the right side, which protrudes through an opening 33 in the holder 49b. Both holders 49 and 49b each have two bolts 21, 23 and 22, 24, which are received into the ducts 38, 40, as is indicated below by (FIGS. 9 to 20) and is described in still more detail.

Figure 6:
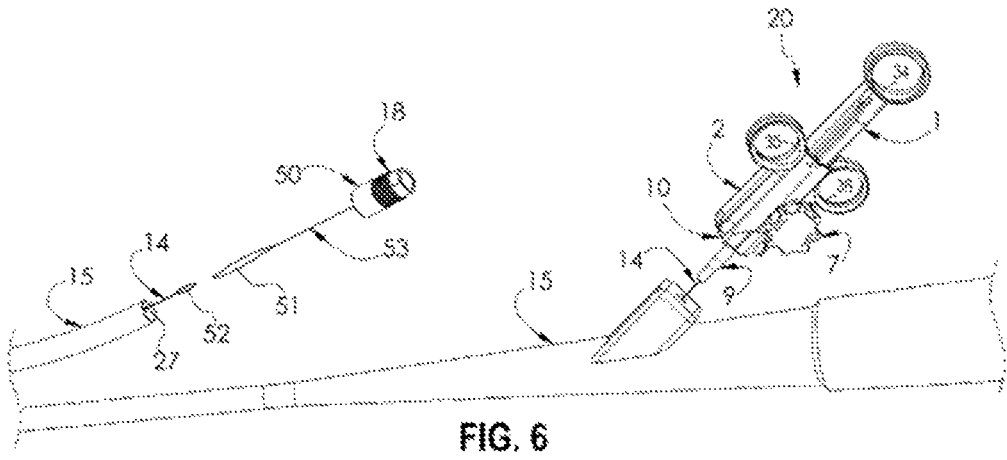
FIG. 6 shows a perspective view of the rubber band ligator in the preparatory stage, with the endoscope and the rubber bands.

Both receiving members 3 and 5 are tightly connected or, for example, adhesively bonded to each other (FIG. 5, 5a, 5b), between these is located the spool 4 onto which is wound the wire 14 that is guided into a pipe 9 (FIG. 1, 6, 8) and an endoscope 15, the endoscope 15 being provided with a camera 27 on one end (FIG. 6).

According to FIGS. 5 and 5a, b, there is a socket 6 with an external gear 6b on the right side of the receiving member 5, which socket receives a pretensioned coil spring 13 in its cavity. The coil spring 13 can be wound or tensioned with the help of a handle 7 according to FIG. 5. The coil spring 13 is fixed in the socket 6 with the help of a holder 28 and is locked with the internal part with the help of the axle (26)

that has the edge surfaces and which, for example, can be designed as a hexagonal connection, by means of which the coil spring 13 can be wound or tensioned during the production stage if the rotary handle 7 is rotated according to the arrow 30 to this end.

Figure 8:
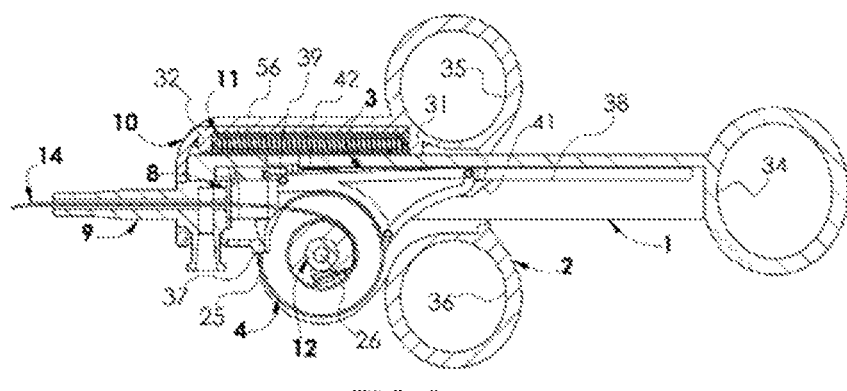
FIG. 8 shows a sectional view of the rubber band ligator in the original state, as well as a wire on a spool and a tension spring in a hollow space.

According to FIGS. 6 and 8, one end of the wire 14 is mounted on the spool 4, and another end is guided into a pipe 9, wherein the pipe 9 is mounted in the endoscope 15.

Figure 3:
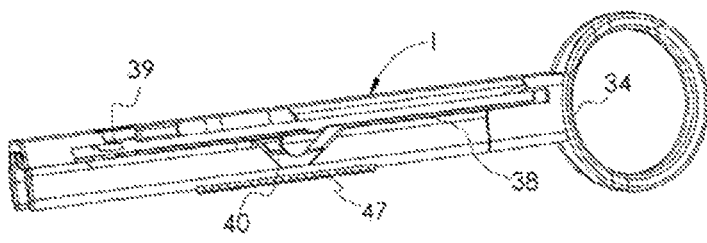
FIG. 3 shows a moving element and an axial element with an upper and lower guide track.

The axial element 1 (FIG. 3, 20) has an upper longitudinal groove 38 and, at a distance to this, a second or lower longitudinal groove 40. Both front ends of the ducts 38 and 40 are connected with each other by means of a connecting duct 54 running sloped in the direction of the pipe 9. Both ducts 38, 40 are connected with each other by means of a connecting duct 55 behind the handles 35, 36 that runs sloped.

Figure 6A:
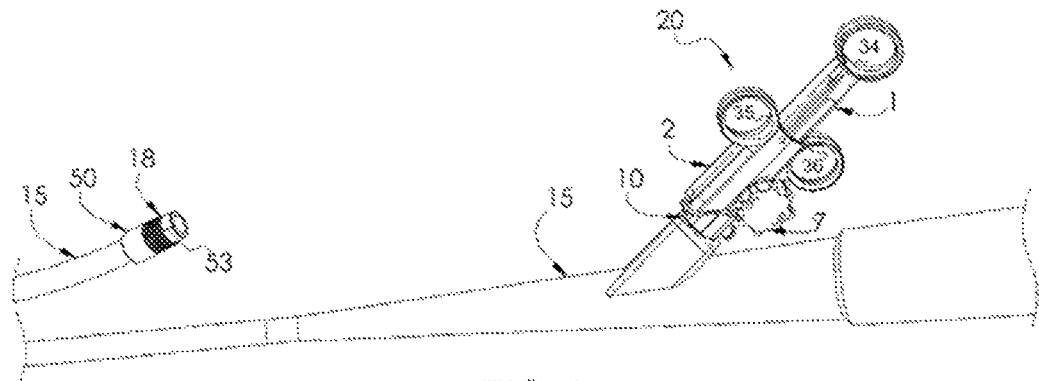
FIG. 6a shows a perspective view of the rubber band ligator in the starting position of the operating stage, with the endoscope and the rubber bands.
Figure 6B:
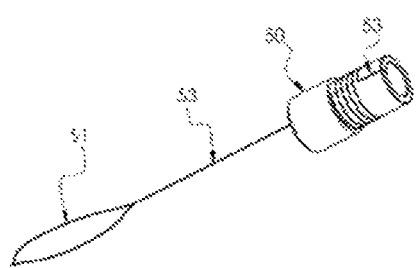
FIG. 6b shows a perspective view of the cap with the thread, without the rubber bands.
Figure 9:
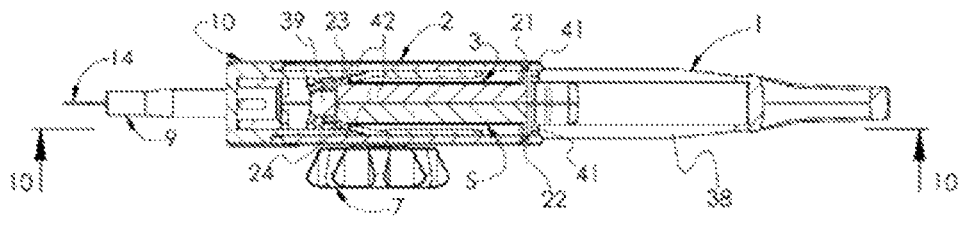
FIG. 9 shows a sectional view of the rubber band ligator in the view from above, as well as elastic pawls, which prevent the bolts moving on the upper longitudinal groove.
Figure 10:
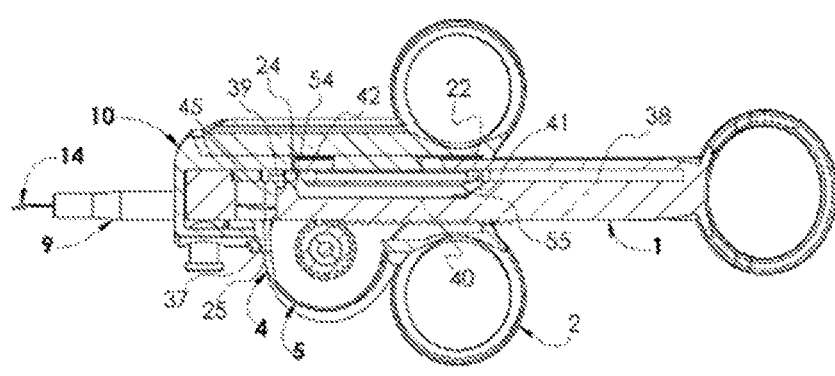
FIG. 10 shows a sectional view of the rubber band ligator in the view from the side in a starting position of the pulling stage, wherein the bolts are guided from the diagonally running front connecting duct into the upper longitudinal groove.
Figure 11:
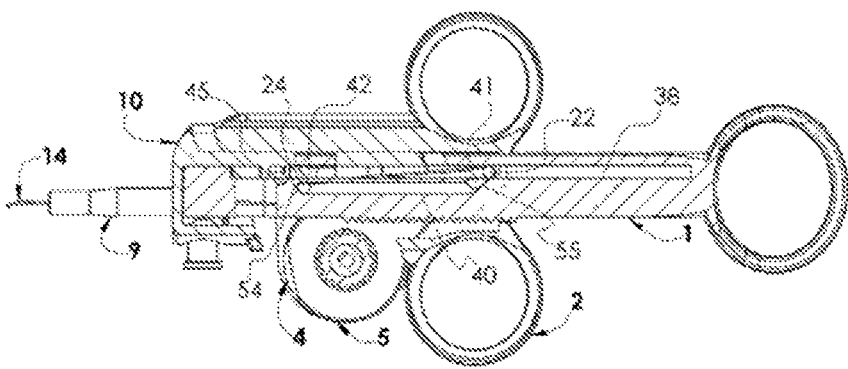
FIG. 11 shows a sectional view of the rubber band ligator in the view from the side in the pulling stage, wherein the bolts are guided from the upper longitudinal groove into the lower longitudinal groove.

The wire 14 is formed as a length such that it protrudes a little from the endoscope 15. A cap 50 is arranged at the end of the endoscope 15 during the preparatory stage (FIG. 6-8), on which several rubber bands 18 are applied. The end of the wire 14 is connected by means of a loop 52 with a loop 51 of a thread 53 which is received into the endoscope 15 and is connected to the spool 4. By means of gently pulling the trigger 2 2 to 3 mm, the winding mechanism is operated, consequently the wire 14 is drawn into the endoscope 15 and the cap 50 is placed on the end of the endoscope 15 (FIG. 6a, 9, 10).

The spool 4 is provided with a locking device 25 (FIG. 5a, 5b, 7, 8), which blocks a rotational movement of the spool 4 as long as the locking device 25 is moved away from the abutment 37 by means of gently pulling the trigger 2 2 to 3 mm backwards in the direction of the handle 34, so that the bolts 23 and 24 are, in the preparatory stage (FIG. 6-10), initially moved upwards and backwards in the connecting duct part 45 that runs diagonally (FIG. 7-10), wherein the bolts 21 and 22 are received into the bores 16 and thereby remain permanently in the upper longitudinal groove 38. By means of pulling the trigger 2 and thus by means of moving it on the axial element 1, the wire 14 is automatically wound onto the spool 4 with the help of the coil spring 13 (FIG. 6a, 9, 10) during the preparatory stage (FIG. 6-10), by means of releasing the abutment 37 provided on the front part 10. To this end it must be noted that the coil spring 13 is received into the socket 6 in the pretensioned state.

Figure 14:
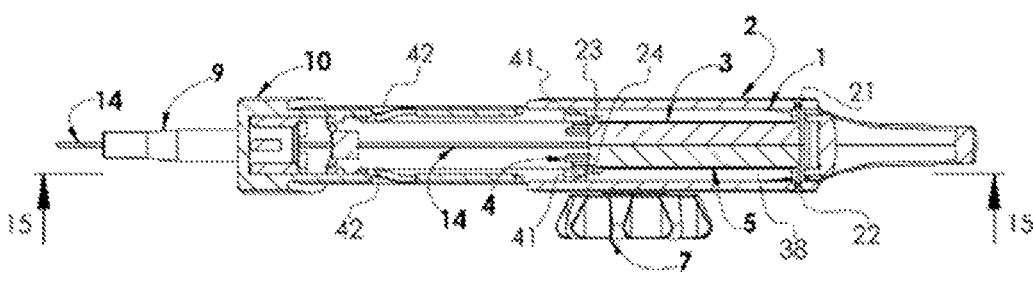
FIG. 14 shows a sectional view of the rubber band ligator in the view from above, in which the two elastic pawls on the side are returned into the original state.
Figure 15:
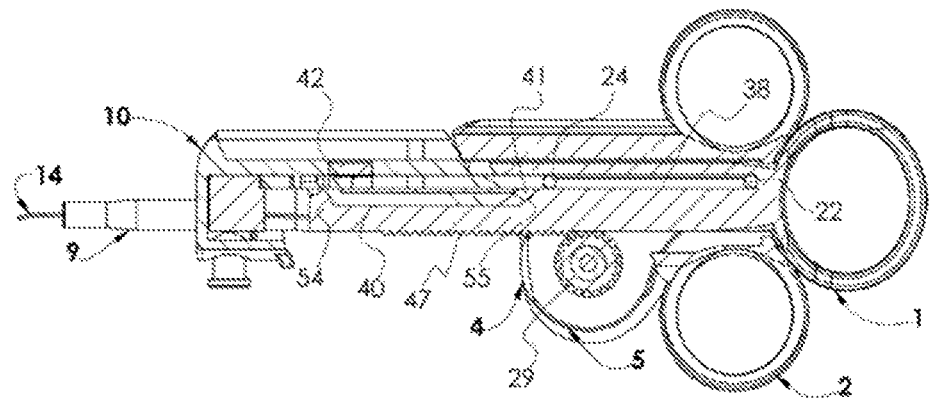
FIG. 15 shows a sectional view of the rubber band ligator in the view from the side, in which the end of the pulling phase of the wire is shown.
Figure 16:
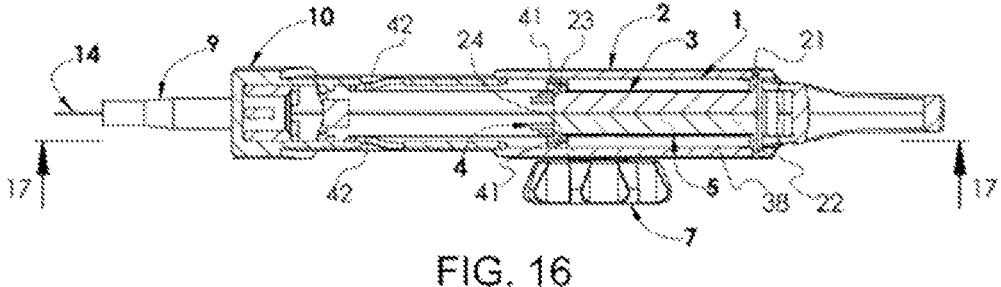
FIG. 16, 17 show a sectional view of the rubber band ligator, wherein the two elastic pawls on the side prevent the bolts returning into the lower longitudinal groove.
Figure 17:
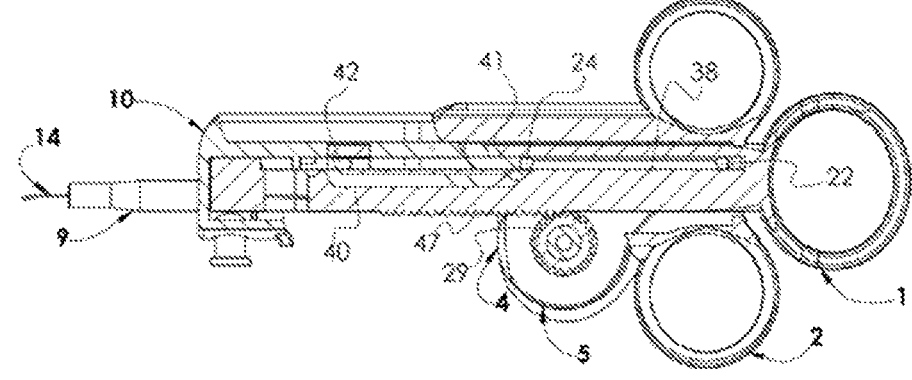
FIG. 17 shows a sectional view of the rubber band ligator in the view from the side; wherein the start of the drive connection between the gear wheel and gear rack is shown.
Figure 18:
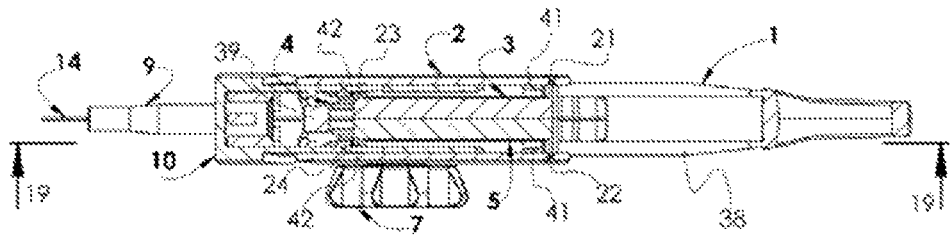
FIG. 18, 19 show a sectional view of the rubber band ligator in the view from above; wherein the bolts push two elastic pawls on the side outwards.
Figure 19:
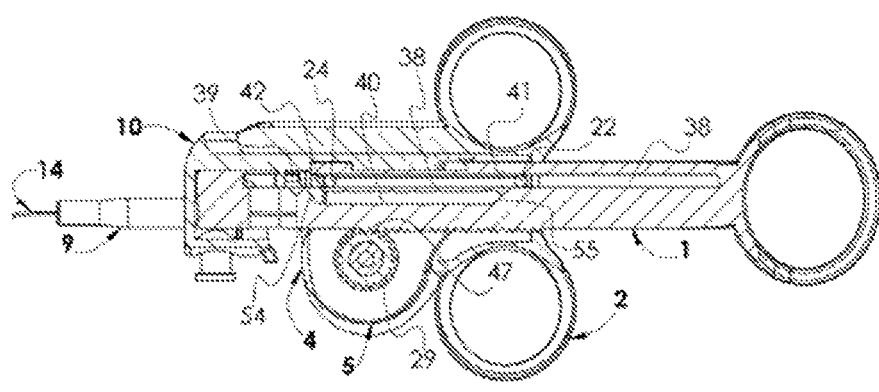
FIG. 19 shows a sectional view of the rubber band ligator in the view from the side; wherein the additional end of the drive connection between the gear wheel and gear rack is shown.

By means of further pulling, the trigger 2 is pulled with the receiving member 3 and the fixed covering 5 and thus the whole assembly 19 (FIG. 5-5b, 9-10) in the direction of the handle 34, wherein the bolts 21 and 22 are moved backwards, are guided through the connecting duct 54 (FIG. 10-11) then into the lower longitudinal groove 40 and the bolts 23, 24 thereby enter the running connecting duct 55 (FIG. 12-13), then the upper longitudinal groove 38 (FIG. 14-15).

Figure 1A:
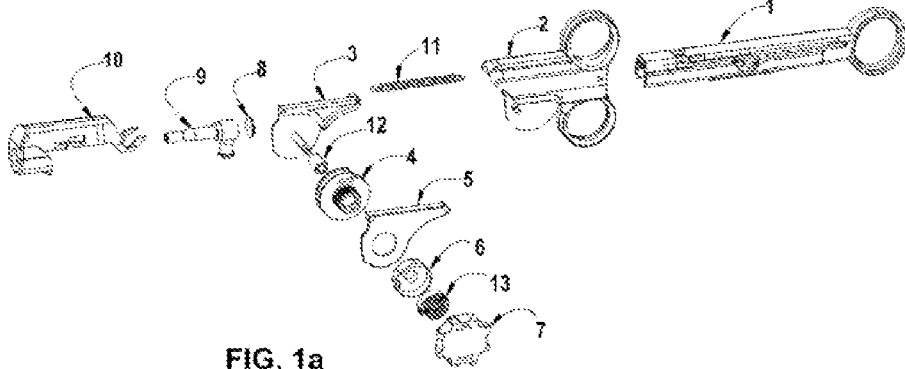
FIG. 1a shows an exploded view of the rubber band ligator.
Figure 2:
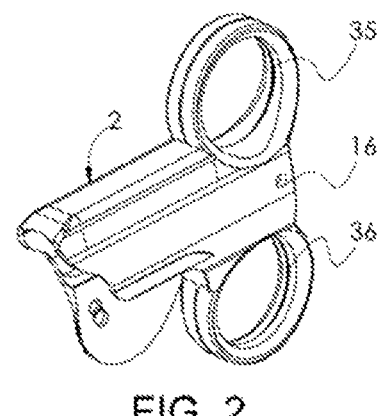
FIG. 2 shows a trigger for operating an automatic winding mechanism and for pulling the wire.
Figure 4:
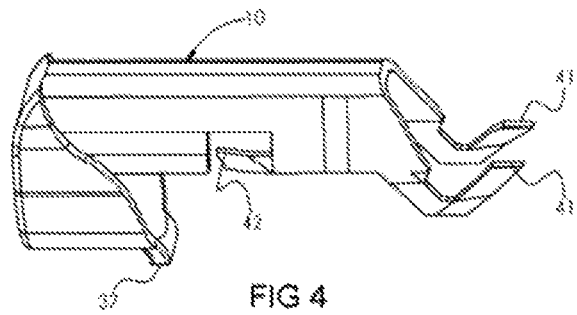
FIG. 4 shows a front part, a locking device with pawls.
Figure 12:
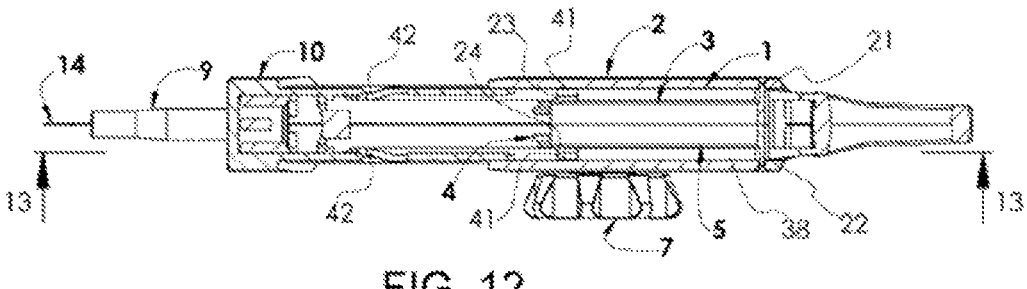
FIG. 12 shows a sectional view of the rubber band ligator in the view from above, wherein the bolts push two elastic pawls on the side outwards.
Figure 13:
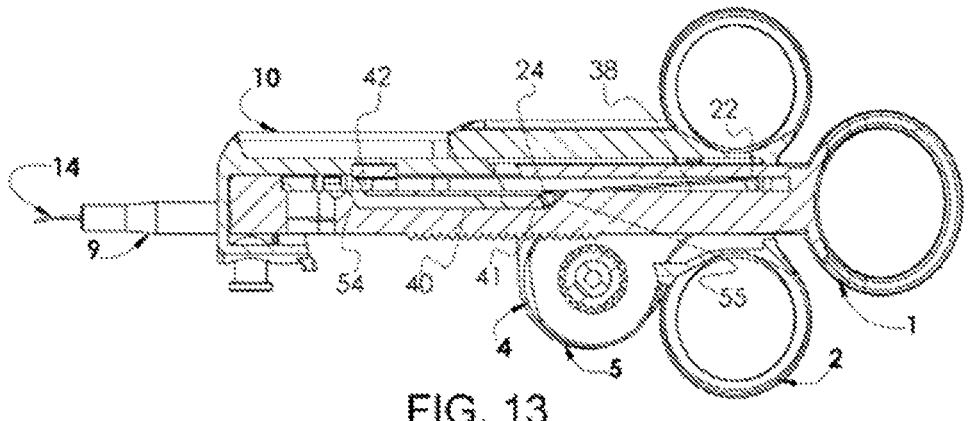
FIG. 13 shows a sectional view of the rubber band ligator in the view from the side, wherein the bolts are positioned in the connecting duct.

According to FIG. 4, the front part 10 of the rubber band ligator in each case in the external area has two elastic pawls 42 on the side, only one of which can be seen in plan view (FIG. 1a, 9), which prevent the bolts 23 and 24 moving backwards in the direction of the handle 34 on the upper longitudinal groove 38 by means of pulling the trigger 2, rather moving through the connecting duct 54, which connects the upper and lower longitudinal groove 38, 40. It is hereby ensured that the bolts 23, 24 are guided into the lower longitudinal groove 40 and the bolts 23, 24 thereby enter into the running connecting duct 55, which connects the lower longitudinal groove 40 with the upper longitudinal groove 38, into the upper longitudinal groove 38, as a result of which the elastic pawls 41 of the front part 10 are pushed outwards (FIG. 12, 13). After the bolts 23, 24 go past the pawls 41, the pawls 41 are moved back into their original state (FIG. 14, 15), It is thus ensured that the bolts 23, 24 do not return to the lower longitudinal groove 40, rather they can be moved into the upper longitudinal groove 38.

According to FIG. 8, a tension spring 11 is provided in a hollow space 56 between the front part 10 and the axial element 1, wherein one end of the tension spring 11 is fixed to the front part 10 by means of a fastening part 32 and, on the other side, is fixed to the trigger 2 by means of a fastening part 31. The tension spring 11 constantly exerts a tensile force on the trigger 2 with the assembly 19 and brings the trigger 2 forward in the direction of the endoscope 15 up to the end of the upper longitudinal groove 38, so that the bolts 23, 24 cannot enter via the running duct 45, since the locking device 39 (FIG. 9, 10) prevents this. The locking device 39 is fixed to the axial element 1 and is situated in the front part of the axial element 1 according to FIG. 3.

By means of returning the trigger 2 and the assembly connected with it, a drive connection between the gear wheel 29 and a gear rack 47 (FIG. 17, 19) which is situated on the lower part of the axial element 1 (FIG. 3) is also produced.

By means of the drive connection between the gear wheel 29 and the gear rack 47, which is provided on the underside of the axial element 1 (FIG. 3, 17-19), the wire 14 is wound onto the spool 4 by returning the trigger 2 and the two pawls 42 of the front part 10 (FIG. 18) are simultaneously pushed outwards, so that the bolts 23, 24 in the upper guide track 38 can no longer reach the back, but rather go down into the lower longitudinal groove 40, via the connecting duct 54. Every time that the trigger 2 is moved backwards, a rubber band is released from the end of the endoscope 15 and is applied to the corresponding part of the patient to be treated.

According to FIG. 6, the thread 53 is connected with numerous rubber bands 18 arranged next to each other on the cap 50, so that by means of respective pulling of the trigger 2, a new rubber band can be applied to the desired part. The operating process of the trigger 2 and the assembly 19 is hereby repeated, as already described.

Summary of the operating process for applying rubber bands 18 to the desired place with the help of the rubber band ligator 20, for example on a hemorrhoid.

The operating process consists of two stages:

1. Preparatory Stage

In the preparatory stage, the rubber band ligator 20 and the rubber bands 18 are mounted on the endoscope 15 with the cap 50 (FIG. 6-10), and the excess length of the wire 14 and of the thread 53 is wound onto the spool 4 by means of activation of the winding mechanism.

2. Operating Stage a) In the pulling stage, the wire 14 is moved by means of pulling the trigger 2 (FIG. 9-15) and the rubber band 18 is consequently released.

b) By means of returning the trigger 2 (FIG. 14-19, 10) into the starting position, the wire 14 is wound onto the spool 4 with the help of the drive connection.

Figure 7:
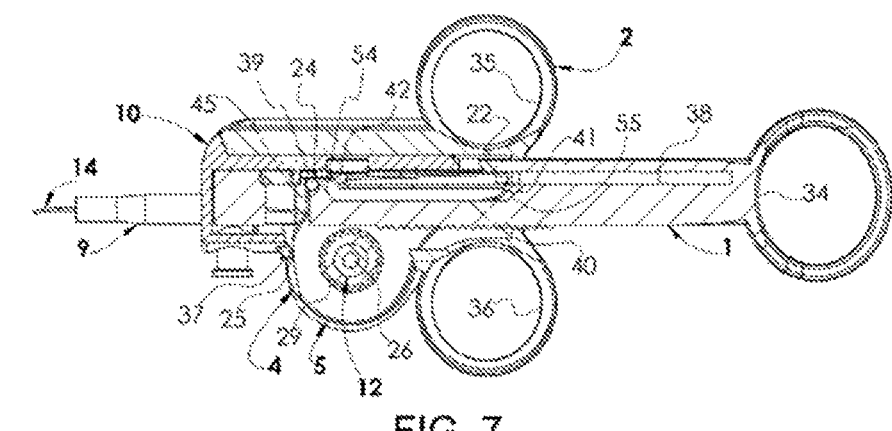
FIG. 7 shows a sectional view of the rubber band ligator, in a view from the side, in the original state.
Figure 7A:
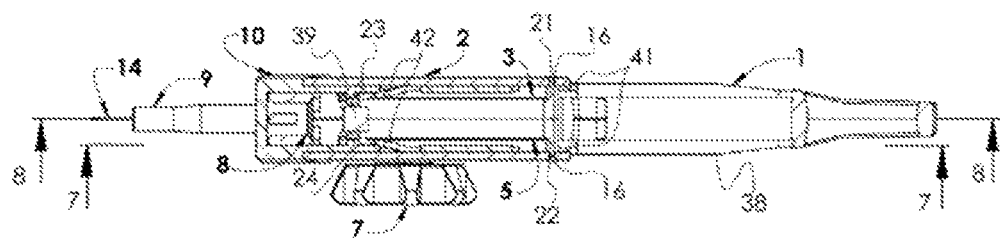
FIG. 7a shows a sectional view of the rubber band ligator, in a view from above, in the original state.

In the preparatory stage, the wire 14 is inserted through the endoscope 15 according to FIG. 6-8 and the rubber band ligator 20 is then mounted on the endoscope 15 by means of inserting the pipe 9 into the endoscope 15.

After the insertion of the wire 14 into the endoscope 15, it is, according to FIG. 6, connected with the thread 53 by means of the loops 51, 52, the thread being connected with the numerous bands 18 placed on the end of the endoscope.

The winding mechanism is then activated by means of operating the trigger 2, i.e. by means of gently pulling the trigger 2 2 to 3 mm, and the locking device 25 of the spool 4 moves away from the abutment 37 of the front part 10 (FIG. 10). The spool 4 is then rotated clockwise with the help of a pretensioned, wound coil spring 13 and the wire 14 is thereby automatically wound onto the spool 4.

At the same time, the bolts 23, 24 move upwards and backwards in the diagonally running connecting duct section 45, from the original state (FIG. 7, 8) to the starting position (FIG. 6a, 10). The locking device 39 is thereby forced to move upwards and to return to the original state. This process produces a tick sounds, which announces the beginning of the automatic winding.

Consequently, the excess length of the wire 14 and of the thread 53 is automatically drawn into the endoscope 15 (FIG. 6) and the cap 50 is applied to the end of the tube of the endoscope 15 (FIG. 6a, 10), so that the rubber band ligator 20 can be used for the operating stage. A rubber band on the end of the endoscope 15 is only released in the desired place and applied to the corresponding part of the patient to be treated.

Next the operating stage begins with pulling the trigger 2 further by approx. 40 mm. The bolts 23 and 24 are thereby drawn backwards in the direction of the handle 34. Since the two elastic pawls 42 on the side of the front part 10 prevent the bolts 23 and 24 entering the upper longitudinal groove 38, the bolts 23, 24 are guided into the lower longitudinal groove 40 via the connecting duct 54. Further, the bolts 23, 24 enter the upper longitudinal groove 38 through the running connecting duct 55, as a result of which the elastic pawls 41 of the front part 10 are pushed outwards (FIG. 12, 13). After the bolts 23, 24 go past the pawls 41, the pawls 41 are returned to their original state (FIG. 14, 15, 20), which ensures that the bolts 23, 24 do not return to the lower longitudinal groove 40, rather remain in the upper longitudinal groove 38. Next, the wire can be pulled and a rubber band 18 is thereby applied to the part to be treated, like varices, and the end of the pulling stage is thus reached.

To this end it must be noted that there is no gearwheel connection between the gear rack 47 and the gear wheel 29 in the pulling stage, since the bolts 23, 24 are situated in the lower longitudinal groove 40 during this stage.

After the first rubber band 18 has been applied, the trigger 2 is returned into its starting position according to FIG. 10 with the help of the tension spring 11.

By means of returning the trigger 2 into its starting position, a drive connection is produced between the gear wheel 29 and a gear rack 47 (FIG. 17-19), this leads to the winding of the wire 14 onto the spool 4. On the stationary end, both pawls 42 of the front part 10 (FIG. 18-19) are pushed outwards and after the bolts 23, 24 have gone past the pawls 42, they are returned to their original state (FIG. 9, 10). It is thus ensured that the bolts 23, 24 are no longer guided backwards in the upper longitudinal groove 38, rather they are guided into the lower longitudinal groove 40 by means of the connecting duct 54.

The first working process is then completed and this work process can now be freely repeated, without the operating person needing to make structural changes to the rubber band ligator 20.

Figure 21:
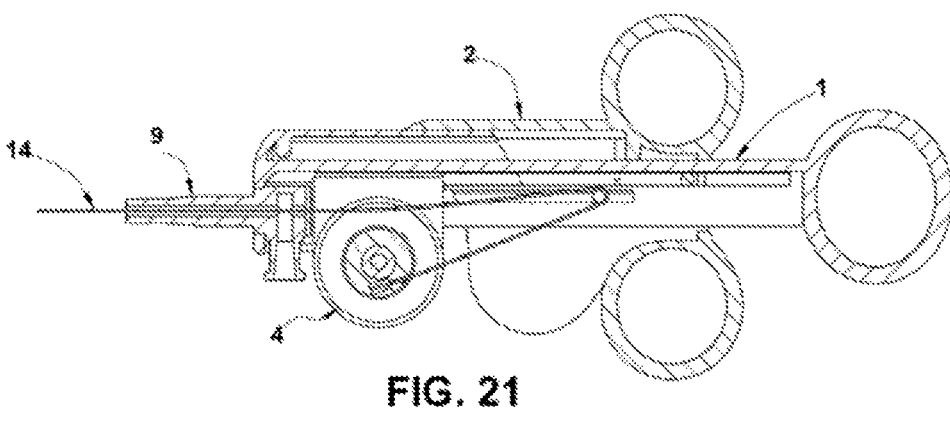
FIG. 21 shows a perspective sectional view of a design of the device, in which the assembly with the spool is arranged on the axial element, wherein the trigger is in a proximal position.

FIG. 21 shows a perspective sectional view of a design of the device, in which the assembly 19 with the spool 4 is arranged on the axial element 1, wherein the trigger is in a proximal position. In this case, the trigger 2 has a catch around which the wire 14 is redirected. An end of the wire is fixed to the spool.

Figure 22:
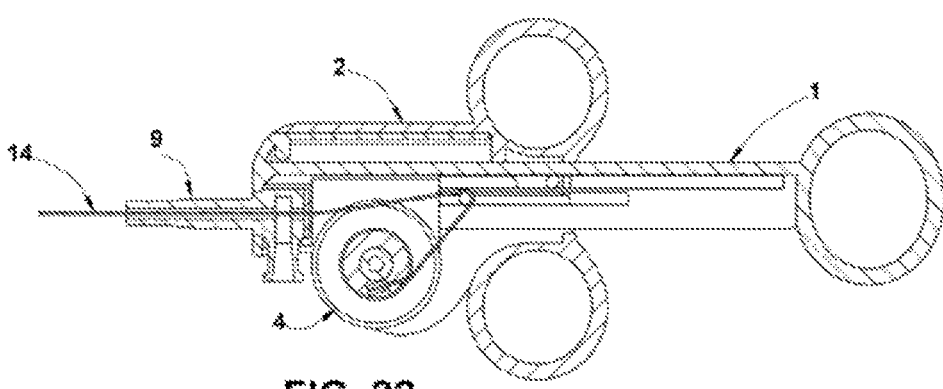
FIG. 22 shows a perspective sectional view of a design of the device, in which the assembly with the spool is arranged on the axial element, wherein the trigger is in a distal position.

FIG. 22 shows a perspective sectional view of the design from FIG. 21, in which the trigger 2 is in a distal position. The spool 4 is driven by a spring, which can, for example, be situated in the interior or on one side of the spool 4. In this embodiment, the winding mechanism is designed such that the spool 4 is automatically wound if the trigger 2 moves from the proximal position into the distal position and the wire thereby slackens. When pulling the trigger 2 in the proximal direction, the spool 4 is, however, blocked by means of a locking device, e.g. by means of a pawl that engages on the spool 4. A gear that converts the forward or backwards movement of the trigger 2 into a rotational movement of the spool 14 is not necessary in this case. Another embodiment of the device shown in FIG. 21, 22 with a spool arranged on the axial element 1 could, however, alternatively be provided with such a gear mechanism.

LIST OF REFERENCE NUMERALS

1 Axial element
2 Trigger
3 Receiving member
4 Spool
4b Arrow
5 Receiving member, mounted covering
6 Socket with external gear 6b for the coil spring 13
6b External Gear
7 Rotary handle
8 Seal
9 Pipe
10 Front part, locking device
11 Tension spring
12 One-way needle bearing
13 Pretensioned wound coil spring, spring
14 Wire
15 Endoscope
16 2 bores in the trigger 2
18 Several rubber bands arranged next to each other on the cap 50
19 Assembly
20 Rubber band ligator
21 Bolt
22 Bolt
23 Bolt
24 Bolt
25 Locking device
26 Axle in the receiving member 3
27 Camera on the end of the endoscope 15
28 Holder in the socket 6
29 Gear wheel
30 Arrow in the handle 7
31 Fastening part for tension spring 11
32 Fastening part for tension spring 11
33 Opening in 48 b
34 Circular handle in the axial element 1
35 Circular handle in the trigger 2
36 Circular handle in the trigger 2
37 Abutment
38 Upper longitudinal groove, duct
39 Locking device
40 Lower longitudinal groove, duct
41 Elastic pawls
42 Elastic pawls
43 Edge surfaces
45 Diagonal front connecting duct, at the end of the ducts 38, 40
47 Gear rack
48 Disc
48b Perforated disc

49 Holder for receiving the bolts 21, 23, receiving member

49b Holder for receiving the bolts 22, 24, receiving member

50 Cap

51 Eyelet for the thread 53, loop

52 Eyelet on the end of the wire 14, loop

53 Thread inside the end of the cap 50

54 Front connecting duct

55 Back connecting duct

56 Hollow space

The invention claimed is:

1. A device for applying rubber bands in the human body and in other living beings, comprising:

a) an axial element (1) having a first handle (34);

b) a trigger (2), which is movably mounted on the axial element (1) and has at least one handle (35, 36) for moving the trigger (2) along the axial element (1), wherein the trigger (2) serves to pull a wire (14);

c) an assembly (19) that has a spool (4) for winding up the wire (14), characterised in that the spool (4) is tightly connected with the trigger (2); and d) a gear mechanism formed in such a way that, when the trigger (2) is pulled, the spool (4) is not rotationally driven and the wire (14) is pulled along by means of the pulling movement of the trigger (2), whereby one or more rubber bands (18) can be applied to a part of a living being to be treated, and that when the trigger (2) moves back into a starting position, the wire (14) is wound onto the spool (4).

2. The device according to claim 1, characterised in that the spool (4) is coupled with the trigger (2) by means of the gear mechanism, which implements a translational movement of the trigger (2) during a rotational movement of the spool (4) and is configured such that the spool (4) is driven rotationally along the axial element (1), at least during a part of the movement of the trigger (2), and winds up the wire (14).

3. The device according to claim 1, characterised in that a spring-actuated winding mechanism is provided that can rotationally drive the spool (4).

4. The device according to claim 3, further comprising a locking device (25) operably associated with the spool (14), wherein activating the winding mechanism by gently pulling the trigger removes an abutment (37) of a front part (10) of the device, wherein the spool (4) is rotated with the help of a pretensioned wound coil spring (13) and the wire (14) is automatically wound onto the spool (4).

5. The device according to claim 4, characterised in that returning the trigger (2) to its starting position, the wire (14) is wound onto the spool (4) and, on a stationary end, two pawls (42) of the front part (10) are pushed outwards, wherein a plurality of bolts (23, 24) return the pawls (42) to their original state after going past the pawls (42) and thus ensure that the plurality of bolts (23, 24) cannot be moved backwards in an upper longitudinal groove (38) defined in the axial element (1), but rather can be moved in a lower longitudinal groove (40) in the axial element (1) through a connecting duct (54).

6. The device according to claim 3, characterised in that in a preparatory stage, the end of the wire (14) is connected by means of a loop (52) with a loop (51) of a thread (53) which is received into an endoscope (15), wherein, by means of gently pulling the trigger (2), the winding mechanism is operated and, as a result, the wire (14) is drawn into the endoscope (15) and a cap (50) is placed on the end of the endoscope (15).

7. The device according to claim 1, characterised in that an automatic winding mechanism is provided, with the help of which the wire (14) can be automatically tensioned, wherein the winding mechanism comprises a spring (13), which rotationally drives the spool (4).

8. The device according to claim 1, characterised in that the axial element (1) has an upper longitudinal groove (38) and a lower longitudinal groove (40), which are connected via a plurality of connecting ducts (54, 55) and serve as guide tracks for a plurality of bolts (21, 22, 23, 24).

9. The device according to claim 1, further comprising a plurality of holders (49, 49b) operably engaged with a plurality of bolts (21-24) that belong to the assembly (19), wherein the plurality of bolts (23, 24) are guided into a plurality of ducts (38, 40) and a plurality of connecting ducts (54, 55) of the axial element (1).

10. The device according to claim 9, characterised in that two of the plurality of bolts (21, 22) are continuously guided into an upper longitudinal groove (38) defined in the axial element (1) and the two other bolts (23, 24) of the plurality of bolts are guided into upper and lower longitudinal grooves (38, 40) in the axial element (1) and the plurality of connecting ducts (54, 55).

11. The device according to claim 9, further comprising an axle (26) arranged on one holder (49) of the plurality of holders which extends through an opening (33) provided in a second holder (49b) of the plurality of holders, wherein, with the help of the axle (26) that has edge surfaces, a coil spring (13), connected to a socket (6) with the help of a third holder (28) of the plurality of holders, is locked in position.

12. The device according to claim 1, further comprising two receiving members (3, 5) spaced parallel relative to one another, wherein one receiving member (3) includes an axle (26) for supporting the spool (4) that the wire (14) can be wound onto by an automatic winding mechanism during a preparatory stage of operating the device and by a drive connection during an operating stage of the device.

13. The device according to claim 1, further comprising a gear rack (47) and a gear wheel (29), wherein when the trigger (2) is returned to the starting position the gear rack (47) and the gear wheel (29) are brought into a drive connection wherein the wire (14) is wound onto the spool (4).

14. The device according to claim 1, further comprising a pipe (9) configured to be received and adjusted into the axial element (1), wherein the wire (14) can be guided into the pipe (9) and the pipe (9) is mounted in an endoscope (15) and connected to the axial element (1) in such a way that, with the help of the wire, the one or more rubber bands can be applied to the desired part of a living being.

15. The device according to claim 1, further comprising a cap (50) arranged on a distal end of the device, on which the one or more rubber bands (18) are mounted.

16. The device according to claim 1, characterised in that the unloading of the one or more rubber bands (18) onto the end of an endoscope (15) occurs with the help of the wire (14), wherein, for unloading the one or more rubber bands (18), the wire (14) covers a distance of about 30 mm to about 50 mm and, to this end, is wound onto the spool (4) by means of returning the trigger (2) to the starting position.

* * * * *